United States Patent [19]

Elkins

[11] 4,227,414
[45] Oct. 14, 1980

[54] LIQUID TESTING KIT

[75] Inventor: Joseph R. Elkins, Brooklyn, N.Y.

[73] Assignee: J & M Instruments Corp., Farmingdale, N.Y.

[21] Appl. No.: 35,330

[22] Filed: May 2, 1979

[51] Int. Cl.³ .............................................. G01N 1/12
[52] U.S. Cl. ............................... 73/425.4 R; 220/264; 324/438; 324/450
[58] Field of Search .......................... 73/354, 425.4 R; 324/438, 450; 220/263, 264

[56] References Cited

U.S. PATENT DOCUMENTS

| 1,511,223 | 10/1924 | Chapelle | 73/425.4 R |
| 2,255,369 | 9/1941 | Spaeth | 73/425.4 R |
| 3,675,491 | 7/1972 | Guillet | 73/425.4 R |
| 4,090,925 | 5/1978 | Jungman | 324/438 |
| 4,103,447 | 8/1978 | Hill | |

Primary Examiner—S. Clement Swisher
Attorney, Agent, or Firm—Natter & Natter

[57] ABSTRACT

A liquid testing kit for determining the pH value of a liquid body at various depths includes a pH tester and a liquid sampling container having a spring-hinged lid. The container is adapted to be lowered to various depths with the lid in open position. The hinge is then remotely triggered to close the lid at the desired depth whereupon the container is removed from the liquid body. A self-seating ridged planar seal is employed between the lid and the container. The removed container can be stood upright, and a plurality of vertical internal supporting webs are dimensioned so as to accommodate a pH test instrument in the container. The hinge includes a crank arm having a support post against which a closing or opening tensile force is applied. The crank arm is pivoted from a first position wherein the tensile force creates an opening moment to a position wherein the post lies on the opposite side of a pivot so that a tensile force at the same post creates a closing moment. A control line which is fixed to the crank arm remote from the pivot is employed for the purpose of lowering the sampling container to the desired level in the liquid and triggering the crank arm to close the lid.

15 Claims, 8 Drawing Figures

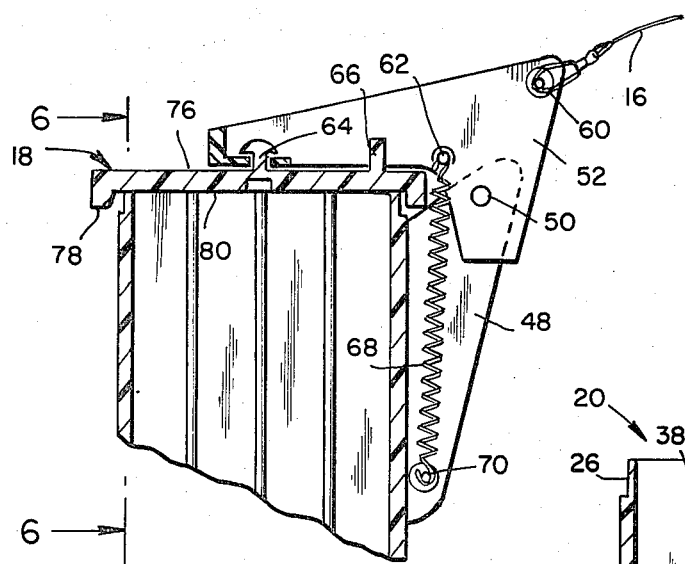
FIG. 5
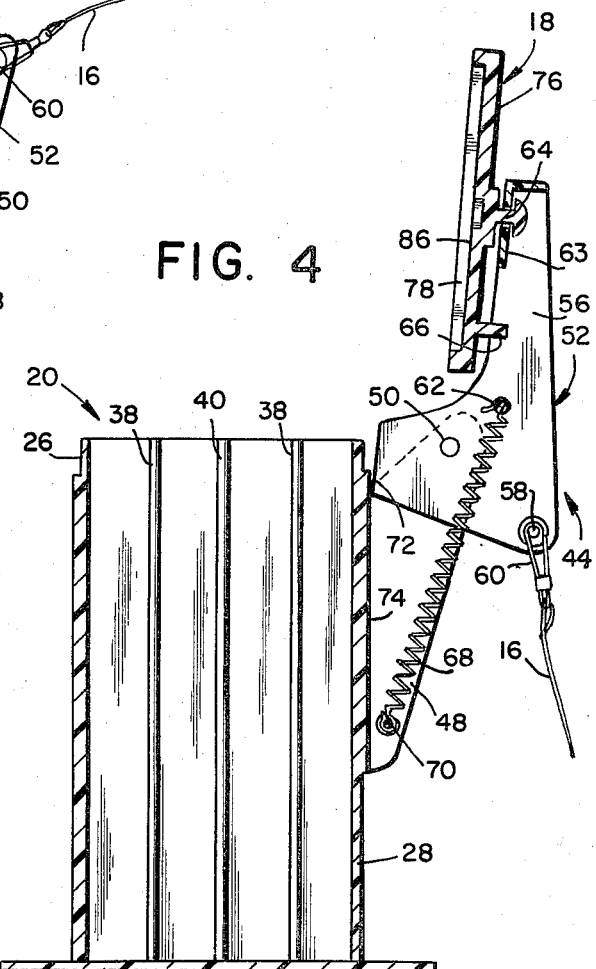
FIG. 4
FIG. 6
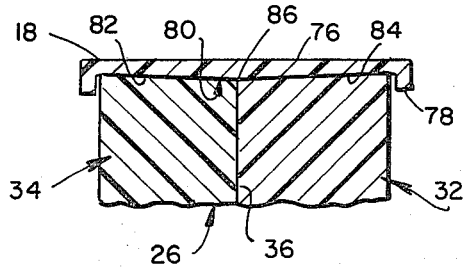
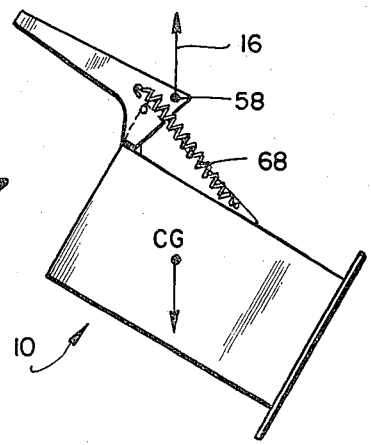
FIG. 7
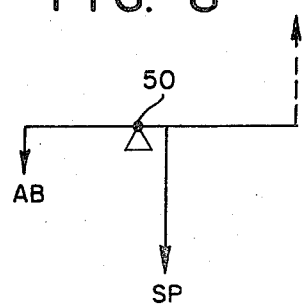
FIG. 8

LIQUID TESTING KIT

BACKGROUND OF THE INVENTION

1. Field of the Invention

The present invention relates generally to liquid testing and more specifically to a sampling container for withdrawing liquid samples from various depths.

2. Brief Description of the Prior Art

Numerous devices have been proposed heretofore for the purpose of obtaining liquid samples for testing purposes. Typically such devices included a sampling container having a closure, means for lowering the container into the liquid and means for remotely actuating the closure to trap liquid in the container.

Many of these prior devices did not provide adequate versatility to meet conditions of particular applications. For example, these devices generally were designed for taking liquid samples over but a limited range of depths. U.S. Pat. Nos. 1,511,223 and 844,433 typified devices using rigid poles for the purpose of lowering the sampling container into a liquid body. The use of lengthy poles necessitated by certain applications resulted in a quite cumbersome procedure, and such devices therefore were deficient except for sampling near the surface.

Other sampling devices employed a rigid rod for the purpose of remotely actuating the container closure and as such suffered from the same limitations with regard to the adaptability for use over various depths.

A further approach toward sampling container design utilized a valve mechanism at the lower end of a container which was intended to permit the entrance of liquid into the container upon descent of the container. The valve mechanism was to seal the container to prevent the withdrawal of the liquid while the container was being lifted. It should be appreciated that, in addition to the disadvantages inherent in valve design and the numerous components employed in conjunction with such valves, these devices did not obtain true indicative samples from varying depths. This was due to the fact that liquid drawn into the bottom of the container on descent of the container tended to remain trapped in the container during further descent. Thus, the liquid samples obtained were not truly representative of the liquid at the depth to which the container was lowered.

Other sampling devices suffered from complexity of operation requiring difficult manipulation and dual controls—one for lowering the container and another for operating the closure.

As a result of the disadvantages of such prior sampling containers, these containers were generally designed for specific applications, e.g. oil tank sampling containers, such as U.S. Pat. Nos. 1,511,223 and 1,544,206, and did not provide adequate versatility for a wide range of applications.

In addition, virtually all liquid sampling containers of this type were designed for the purpose of retrieving a liquid sample which was then transferred to a breaker or other suitable container to proceed with the various tests to be conducted. This procedure inhibited immediate on site determinations, introduced additional sources of error, and required additional laboratory equipment to be used and cleansed.

SUMMARY OF THE INVENTION

The invention comprises a liquid testing kit for determination of a physical characteristic of a liquid body including a test instrument and a sampling container which is adapted to be lowered into the liquid body. The container includes a self-seating lid loosely mounted to a spring-biased trigger hinge. The trigger hinge includes a pivoted crank arm which carries the lid.

A coil spring applies a tensile force to the crank arm at a support post, and the crank arm is pivoted from a first position with the container open and the spring force creating a moment biasing the arm in the first position to a position wherein the post lies on the opposite side of the pivot such that the same spring force creates an opposite moment to close the lid. The triggering force is applied to the crank arm by jerking a control line which is employed for the dual purpose of actuating the hinge and lowering the container to the desired location.

The lid includes a composite ridged surface comprising a pair of intersecting planes and a peripheral lip. The peripheral lip frames the sealing surface to a dimension slightly larger than the periphery of the upper edge of the container. In addition, the edges of the walls of the container at the mouth are configured with a slight taper to match the V taper of the intersecting planes of the sealing surface.

An enlarged base permits the retrieved container to be stood upright, and with the lid opened a pH test instrument can be inserted directly into the container and a measurement taken.

From the above compendium, it will be appreciated that it is an object of the present invention to provide a liquid testing kit of the general character described which is not subject to the disadvantages of the prior art as aforementioned.

A further object of the present invention is to provide a liquid testing kit of the general character described which includes a liquid sampling container which is simple to use and adapted for employment over a wide range of sampling depths.

Another object of the present invention is to provide a liquid sampling container of the general character described which utilizes a single line for both positioning the container in the liquid body and for controlling a lid hinge to remotely close the container.

Another object of the present invention is to provide a liquid sampling container of the general character described which is suitable for low cost, mass production fabrication.

A still further object of the present invention is to provide a liquid sampling container of the general character described which is adapted to hold and support a test instrument without the necessity of transferring the retrieved liquid for testing purposes.

Yet another object of the present invention is to provide a liquid sampling container of the general character described which includes a spring hinge for remotely closing the container lid through actuation of a single line used to position the container within a liquid body.

Other objects of the present invention in part will be obvious and in part will be pointed out hereinafter.

With these ends in view, the invention finds embodiment in certain combinations of elements and arrangements of parts and series of steps by which the objects aforementioned and certain other objects are hereinafter attained, all as fully described with reference to the accompanying drawings and the scope of which is more particularly pointed out and indicated in the appended claims.

BRIEF DESCRIPTION OF THE DRAWINGS

In the accompanying drawings in which is shown one of the various possible exemplary embodiments of the invention:

FIG. 4 is a representative sectional view through the container with the lid open, the same being taken substantially along the line 4—4 of FIG. 3 and better illustrating the crank pivot and the manner in which the crank arm is prevented from further rotation under the influence of the coil spring by abutment between the crank arm and a container wall;

FIG. 5 is an auxiliary sectional view similar to that of FIG. 4, however the lid is shown in closed position;

FIG. 6 is a full scale sectional view through the container with the lid closed, the same being taken substantially along the line 6—6 of FIG. 5 with portions deleted for clarity, and showing the sealing surface of the lid formed as a pair of intersecting planes and a mating taper along the edges of the container mouth;

FIG. 7 is a schematized, reduced scale, elevational view of the container being supported by a line fixed to the crank arm and being lowered into a liquid body with portions of the container deleted; and FIG. 8 is a force diagram depicting the representative static moments applied about the crank arm pivot and illustrating in dashed lines a triggering force being applied through the supporting line to rotate the crank arm about the pivot to reverse the moment created by the coil spring and close the lid.

DESCRIPTION OF THE PREFERRED EMBODIMENT

Figure 1:
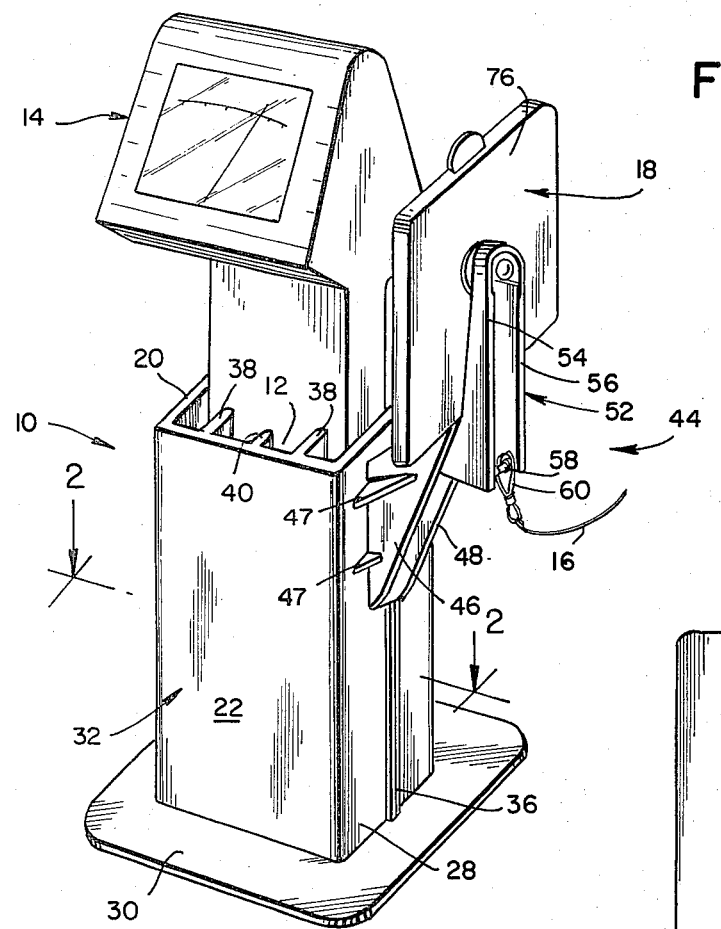
FIG. 1 is a perspective illustration of a liquid testing kit constructed in accordance with and embodying the present invention and showing a container in an upright position and carrying a pH test instrument for the purpose of determining the pH value of a sample withdrawn from a liquid body.

Referring now in detail to the drawings, the reference numeral 10 denotes generally a liquid sampling container constructed in accordance with and embodying the present invention. From an observation of FIG. 1 it will be seen that the container 10 is adapted to retrieve and contain a sample of liquid 12 and accommodate a liquid testing instrument 14 such as the pH test instrument disclosed in U.S. Pat. No. 4,090,025 issued May 23, 1978 to Jungman and assigned to the assignee of the present invention. As will be described in detail hereinafter, the container 10 is adapted to be lowered into a liquid body while being supported from a thin flexible line 16. When the container has completed its descent to the desired depth the line 16 is manipulated to close a lid 18 and seal the container 10, whereupon the container is lifted from the liquid body.

The container 10 comprises an upright liquid sampling vessel having an open mouth 20 which is selectively closed by the lid 18. In an exemplary manner, the container is formed by a pair of parallel spaced front and rear walls 22, 24, respectively, which are joined by a like pair of parallel spaced side walls 26, 28. It should be appreciated that the upright rectangular boxlike configuration as shown in the drawings is merely one of many possible shapes. Accordingly, the container can be formed by cylindrical, spherical, cubic, or other configuration. A bottom closure for the container is provided by a base 30 which extends between the side, front and rear walls.

The container 20 is adapted to descend into the liquid body in a canted rather than upright position so that the mouth 20 is at an angle other than horizontal. Such orientation permits ready entrance of liquid through the mouth and into the vessel. Further, the canted orientation provides, during sampling, a shallow depth to the vessel and thus facilitates ready comingling of the liquid in the vessel with the surrounding liquid during descent. When the container reaches the desired depth, all of the liquid in the vessel is representative of the surrounding liquid of the body at such depth.

In contrast, if the container 10 descends vertically, the effective area of the mouth 20 is substantially reduced and there is a possibility that the liquid initially collected in the container base may be disproportionately representative of a sampling at the surface when insufficient dwell time is provided at the sampling depth and the container is immediately closed and removed.

For the purpose of preventing the container from tipping over when stood upright, especially with the test instrument 14 positioned in the container, the base 30 desirably extends beyond the boundaries of the container walls. As will be explained hereinafter, the enlarged base additionally serves to provide restraintive force which facilitates closing the lid 18 when the container is positioned with a liquid body.

The container 10 may be formed of various thermoplastics such as acrylonitrile-butadiene-styrene and injection molded in the form of two shell halves 32, 34 which are subsequently joined together along a vertical seam 36. The seam 36 extends vertically along the side walls 26, 28 and across the base 30. A liquid tight seal along the seam 36 is effected through the use of commonly available organic solvent cements. As can be observed in FIG. 2, the side walls 26, 28 are preferably thickened adjacent the seam 36 for the purpose of strengthening the container structure and providing an enlarged sealing surface.

In order to nestably receive the test instrument 14 in an erect position within the container, a plurality of integral vertical ribs 38, 40 project from the front and rear walls 22, 24 toward one another. The space between the opposed ribs 38 is sightly greater than the width of a probe portion of the test instrument 14 so that the test instrument 14 will be maintained upright within the container 10.

Figure 2:
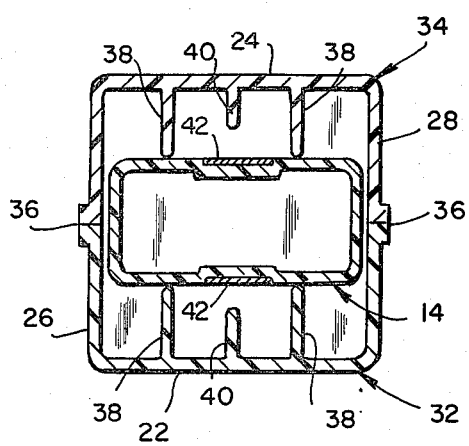
FIG. 2 is a sectional view through the container and test instrument taken substantially along the plane 2—2 of FIG. 1 with portions of the test instrument and container deleted for simplicity.

From an observation of FIG. 2, it will be appreciated that the opposed ribs 40 which are positioned intermediate the ribs 38 provide a greater clearance. This is for the purpose of permitting complete liquid contact with a pair of electrodes 42 which are mounted on the test instrument probe.

It should be appreciated from the foregoing that the liquid sampling container 10 is not only adapted to retrieve a liquid sample from a desired depth but, in addition, is specifically designed to receive the test instrument 14 so that an immediate in situ measurement of the retrieved liquid sample can be obtained. Thus, the necessity of having additional vessels for the use in obtaining test data has been obviated.

Figure 3:
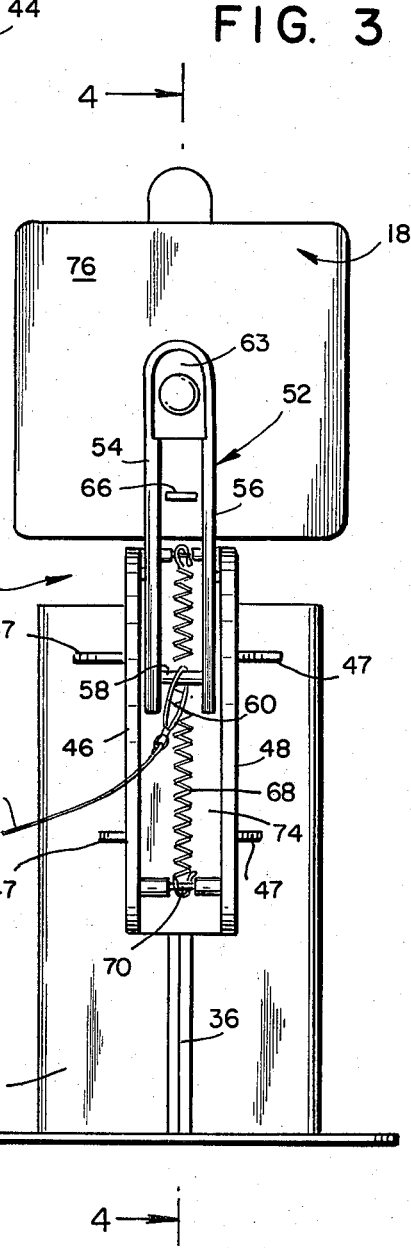
FIG. 3 is a full scale side view of the container showing a lid hinge mechanism including a coil spring secured between the container wall and a post formed in a crank arm of the hinge.

A further aspect of the present invention resides in the manner in which the container lid 18 is remotely actuated. The lid 18 is mounted to a spring biased hinge mechanism denoted generally by the numeral 44 and includes a pair of generally triangular, planar flanges which extend perpendicularly from the side wall 28 on opposite sides of the seam 36. The flanges 46, 48 serve to support and guide a crank arm 52 which carries the lid 18. As will be observed from FIGS. 3 and 4, the crank arm 52 includes a pair of spaced parallel panels 54, 56 between the flanges 46, 48 with each panel being pivotally mounted to its adjacent flange by a pin 50. Separate pins 50 are provided to mount each panel to its respective flange with both pins 50 registered yet spaced apart.

Adjacent the pins 50, the panels 54, 56 are maintained in spaced-apart relationship by an end post 58. The flexible line 16 is anchored to the post 58 through a suitable link such as a ring 60.

A further post 62 straddles the panels 54, 56 adjacent the pins 50 and at at a distance from the pins 50 considerably less than the distance between the pins 50 and the end post 58. The post 62 is seated within enlarged hubs which project from opposite panels 54, 56 toward one another and is adapted to serve as a spring mount.

As illustrated in FIG. 4, a unitary crank arm bridge 63 spans between the panels 54, 56 forming an upper end tip. The bridge 62 includes an aperture adapted to receive a mounting post 64 which projects from the lid 18.

To assemble the container, the lid post 64 is registered with the bridge aperture, while a pilot 66 which projects from the lid 18 is registered between the panels 54, 56. Thereafter, the post 64 is inserted through the bridge aperture and its head is peened to prevent removal. This can be easily achieved with the application of a heated tool to the post 64, assuming the lid 18 is formed of a thermoplastic.

Adequate clearance is provided between the post 64 and the bridge aperture as well as between the pilot 66 and the crank arm panels 54, 56 in order to achieve a loose fit between the crank arm and the lid so that the lid will seat itself over the container mouth. The pilot 66 engages the panels 54, 56 to prevent excessive play.

As mentioned heretofore, the post 62 serves as a spring anchor and accordingly receives one end of a coil spring 68 which extends between the crank arm panels 54, 56 and between the flanges 46, 48. The opposite end of the spring 68 is anchored to a post 70 which extends between enlarged hubs formed at the lower ends of the flanges 46, 48.

With the crank arm in the position shown in FIG. 4, the spring tensile force applied at the post 62 will create a clockwise moment (as viewed in FIG. 4) about the pivot pins 50 tending to maintain the lid 18 in its open position. Clockwise movement of the crank arm 52 beyond the position depicted in FIG. 4 is inhibited by a balancing counterclockwise moment effected by the abutment between an edge 72 of each crank arm panel and a thickened zone 74 of the side wall 28 which spans between the flanges 46, 48.

In such position the empty container 10 may be immersed into a liquid body by lowering the flexible line 16 into the liquid. In the schematized diagram of FIG. 7, the container 10 is shown immersed in the liquid body and supported by the flexible line 16.

With the container 10 supported only by the flexible line 16, a canted orientation is assumed and the center of gravity (denoted CG in FIG. 7) lies directly beneath the post 58 to which the line 16 is attached. In such position the static moments about the pivot pins 50 are in equilibrium, with the counterclockwise moment generated by the spring force (denoted SP in FIG. 8) being balanced by the clockwise moment generated by the abutment force (denoted AB in FIG. 8).

To obtain a liquid specimen, the flexible line 16 is lowered into the liquid body until the container 10 reaches the desired depth after which the line 16 is manipulated to trigger the hinge mechanism 44 and close the lid 18. The triggering procedure is effected by applying a jerking upward force to the line 16 to create a transient dynamic counterclockwise moment about the pivot pins 50. This force is depicted with a dashed arrow in FIG. 8.

It has been found that a static force in the order of two pounds is sufficient in order to rotate the crank arm 52 in a closing direction against the bias of the spring 68. With the container 10 immersed in the liquid, resistance to such dynamic jerking force is provided by the mass of the liquid within the container. Such resistance to acceleration is enhanced by the flange of the base 30 which extends beyond the boundaries of the container wall. Thus, the container tends to remain fixed in its environment, and the sudden force will pivot the crank arm rather than lift the container.

The container 10 resists the transient upward force with the liquid body acting to dampen upward movement of the container thus permitting the jerking force to create a sufficient counterclockwise moment about the pins 50. The crank arm 52 thus begins to rotate in a counterclockwise direction. Initial counterclockwise rotation of the crank arm provides accurate translational movement of the spring anchor post 62 about the pin 50 to a point where the post 62 extends in a line with the spring 70 and the hinge pins 50. The spring 68 itself passes through the space between the two registered pivot pins 50. Further counterclockwise rotation shifts the post 62 to the left of the pivot pins 50 so that the moment created by the spring force becomes a counterclockwise moment which tends to pivot the crank arm 52 to snap the lid 18 against the mouth 20 of the container 10.

Upon initial movement of the crank arm from the open (FIG. 7) position, the counterclockwise moment generated by the abutment force AB is removed because the crank arm is no longer in abutment against the container side wall. Because of the proximity between the spring anchor post 62 and the pivot pins 50, only very slight rotation of the crank arm is necessary to reverse the moment created by the spring force and thus trigger the hinge mechanism 44 to close the lid.

With reference now to FIGS. 4 through 6 it will be seen that the lid 18 is preferably formed of one piece construction and includes a generally planar rear face 76 from which the post 64 and the pilot 66 project to loosely engage the crank arm 52. The lid 18 has the general plan configuration of the periphery of the container 10; hence if the container 10 is of generally square transverse cross section, the lid 18 is of mating configuration.

A depending peripheral lip 78 distends from the rear face as can be seen in FIGS. 5 and 6 and is dimensioned slightly larger than the mouth of the container 10.

In order to provide a self-seating, liquidtight, snap action seal between the lid 18 and the edges of the container mouth 20, a ridged sealing surface 80 is provided on the inner face of the lid 18. The ridged sealing surface 80 is of a configuration generated by a pair of planes 82, 84 which intersect along a central longitudinal ridge 86, with the ridge 86 desirably in registration with the longitudinal seams 36 of the container 10 i.e. plane 4—4 of FIG. 3.

The planes 82, 84 are slightly canted, e.g. 2 degrees from the horizontal, and the edges of the container mouth 20 are matingly canted so that, when the spring 68 snaps the lid 18 over the mouth 20, the ridge 86 will desirably gravitate to the low points of the mouth at the seams 36, and the sealing surface 80 will thus seat against the edges of the mouth 20.

A liquid specimen truly representative of the liquid at the depth to which the container 10 was lowered can thus be obtained. The seal effected assures not only against comingling of liquids while the container is drawn up but, in addition, prevents inadvertent spillage of the specimen during and after removal of the container from the liquid body.

Applicant has found that the sampling container 10 is particularly well adapted for obtaining specimens of liquid from a large body of water at various depths and locations and for rendering pH determinations of such water specimens.

The judicious employment of pH readings thus obtained has proven quite beneficial for anticipating locations wherein various fish have a propensity for congregating. It may well be appreciated that the flexible line 16 which is to be employed in lowering the container 10 and triggering the hinge mechanism 44 may very well comprise a fishing line and, as such, pH determinations can be made within the body of water over the entire range of the fisherman's available line length.

Applicant's sampling kit has thus been found to be a quite useful device to assure successful fresh water fishing. It has been established that bass, for example, prefer and gravitate to a fresh water zone within a pH range of 6.7 to 9.6 with the ideal range between 7.5 and 7.9. In order of priority, bass tend to congregate at locations which firstly have the desired pH range, secondly are within the desired temperature range, and thirdly include an oxygen content within a desired range. Thus, fish may very well congregate in areas where oxygen or temperature conditions are not ideal but where the pH is in the desirable range.

In accordance with the present invention, random readings may be taken at various depths and surface locations prior to fishing in order to determine areas which do not have pH values within the desired range. The readings are taken utilizing the technique of the present invention and employing the fishing line for lowering the container 10, triggering the hinge mechanism 44 and then raising the container.

After the areas of desired pH value have been determined, the sportsman thereafter proceeds to fish in the conventional manner making note of the specific depths at which the desired pH range has been found and prudently fishes only in such areas.

It should be noted that the sampling container 10 is equally suitable for sampling other liquids for different purposes and for rendering various analyses of the liquid content.

Thus, it will be seen that there is provided a liquid testing kit which achieves the object of the present invention and is well adapted to meet the conditions of practical use.

As various changes might be made in the invention as above set forth, it is to be understood that all matter herein described or shown in the accompanying drawings is to be interpreted as illustrative and not in a limiting sense.

Having thus described the invention, there is claimed as new and desired to be secured by Letters Patent of the United States:

1. A kit for rendering an in situ property measurement of a liquid, said kit comprising a vessel adapted to be lowered into the liquid, the vessel having an open mouth for receiving a specimen of the liquid and an instrument for measuring the liquid property, the vessel being so dimensioned as to accommodatingly receive the instrument, the vessel including a plurality of ribs projecting inwardly and defining an area for supporting the instrument, the instrument including a pair of electrodes, the ribs being spaced from the electrodes so as to permit intimate contact between the liquid specimen and the electrodes whereby accurate measurement is facilitated.

2. A kit for rendering liquid property determinations as constructed in accordance with claim 1 wherein the instrument comprises a pH testing instrument.

3. A sampling container adapted to be suspended from a flexible line for the collection of liquid specimens at various depths in a liquid body, the container including a vessel having an open mouth and closure means, the closure means comprising a lid for sealing the mouth and hinge means interconnecting the lid and the vessel, the hinge means including lid carrying means, pivot means rotatively mounting the carrying means, biasing means for maintaining the lid in an open position, and means for reversing the bias of the biasing means to remotely close the lid over the mouth, the carrying means including means for attachment of the line, the attachment means being spaced from the axis of the pivot means.

4. A sampling container constructed in accordance with claim 1 wherein the biasing means applies a biasing force to the carrying means at a point spaced from the axis of the pivot means, the point being spaced from the axis of the pivot means a distance less than the distance between the axis of the pivot means and the attachment means, the biasing means generating a moment about the axis of the pivot means to maintain the lid in an open position.

5. A sampling container constructed in accordance with claim 6 wherein the means for reversing the bias of the biasing means includes means for rotating the carrying means about the axis of the pivot means to effect translational movement of the point across the axis of the pivot means whereby the opening moment of the biasing means is reversed to close the lid.

6. A sampling container constructed in accordance with claim 7 wherein the means for reversing the bias of the biasing means comprises means for applying for applying a dynamic force to the carrying means.

7. A sampling container constructed in accordance with claim 8 wherein the dynamic force is applied at the attachment means, the reversing means further including a flexible line, the flexible line engaging the carrying means at the attachment means.

8. A sampling container constructed in accordance with claim 7 further including means fixing the vessel relative to the carrying means in the presence of a dynamic force applied to the carrying means, the fixing means comprising a flange projecting from the periphery of the vessel and adapted to engage the liquid body.

9. A method of measuring the pH value of a specimen with a container constructed in accordance with claim 3 and a pH test instrument having a pair of electrodes, the method comprising the steps of
 (a) placing liquid in the vessel by lowering the vessel into a liquid body to a desired level,
 (b) closing the lid over the vessel mouth,
 (c) removing the vessel from the liquid body,
 (d) opening the mouth with the vessel in an upright position,
 (e) placing the electrodes of the pH testing instrument into the vessel, and
 (f) observing the pH measurement of the instrument.

10. A method of measuring the pH value of a specimen in accordance with claim 9 wherein the vessel is elongate and the mouth is formed at the upper end of the vessel, the vessel being lowered into the liquid body in a canted position.

11. A method of fishing in accordance with claim 9 wherein the liquid body is a body of water, the method including the further steps of
 (g) obtaining and observing the pH measurement of liquid samples drawn at different depths and from different areas over the surface of the liquid body,
 (h) noting the depth and areas wherein the observed pH measurements fall within a desired range, and
 (i) fishing only in the noted areas and depths.

12. A method of fishing in accordance with claim 11 further including the step of supporting the vessel from a fishing line, the steps of lowering the vessel into the liquid body being conducted by lowering the fishing line, the step of removing the vessel from the liquid being conducted by raising the vessel from the liquid with the fishing line.

13. A container for sampling and holding various liquids, the container including a vessel having an open mouth, a lid for selectively closing the mouth, and hinge means interconnecting the lid and the vessel, the hinge means including lid carrying means and pivot means rotatively mounting the carrying means, means mounting the lid to the carrying means for limited movement with respect to the carrying means, the lid including a sealing surface in selective engagement with the mouth, the sealing surface comprising a pair of planes intersecting along a ridge, the mouth of the vessel being defined by a continuous edge, the edge being shaped in conformity with the intersecting planes of the sealing surface, whereby the loose engagement between the lid and the carrying means permits the sealing surface to seat itself on the edge of the mouth when the lid is closed.

14. A sampling container constructed in accordance with claim 13 wherein the hinge means includes biasing means for remotely closing the lid and maintaining the lid with its sealing surface abutting the mouth edge.

15. A sampling container constructed in accordance with claim 14 wherein the hinge means includes means for directing the biasing force of the spring means to selectively maintain the lid in an open position.

* * * * *